United States Patent [19]

Hara

[11] Patent Number: 4,885,696

[45] Date of Patent: Dec. 5, 1989

[54] SIGNAL PROCESSING METHOD FOR DETERMINING BASE SEQUENCE OF NUCLEIC ACID

[75] Inventor: Makoto Hara, Minami-ashigari, Japan

[73] Assignee: Fuji Photo Film Co., Ltd., Kanagawa, Japan

[21] Appl. No.: 30,062

[22] Filed: Mar. 25, 1987

[30] Foreign Application Priority Data

Mar. 26, 1986 [JP] Japan ................................. 61-69074
Feb. 4, 1987 [JP] Japan ................................. 62-25010

[51] Int. Cl.⁴ ...................... G06F 15/46; G01N 31/00
[52] U.S. Cl. .............................. 364/497; 364/413.01; 364/496; 435/6; 436/94
[58] Field of Search .................. 364/413.01, 496, 497; 435/6; 250/303, 484.1 B, 327.2 A, 327.2 C, 327.2 D; 935/77; 436/94

[56] References Cited

U.S. PATENT DOCUMENTS

| | | | |
|---|---|---|---|
| 4,617,468 | 10/1986 | Shiraishi et al. | 250/327.2 A |
| 4,629,891 | 12/1986 | Nakajima et al. | 250/484.1 B |
| 4,665,312 | 5/1987 | Shiraishi et al. | 250/327.2 D |
| 4,706,192 | 11/1987 | Nasu et al. | 364/413.01 |
| 4,720,786 | 1/1988 | Hara | 363/413.01 |
| 4,734,581 | 3/1988 | Hashiue | 250/327.2 C |
| 4,748,326 | 5/1988 | Mori et al. | 250/484.1 B |
| 4,777,597 | 10/1988 | Shiraishi et al. | 364/413.01 |

Primary Examiner—Parshotam S. Lall
Assistant Examiner—Kevin J. Teska
Attorney, Agent, or Firm—Sixbey, Friedman, Leedom & Ferguson

[57] ABSTRACT

A signal processing method for determining the base sequence of nucleic acids from data on an autoradiograph is provided. An autoradiograph including a plurality of resolved rows is formed by resolving a mixture of base-specific DNA fragments or base-specific RNA fragments that have been labeled with a radioactive element in a one-dimensional direction on a support medium. The method detects bands along each resolved row corresponding to the nucleic acid bases from digital signal data representing position and signal level for each row. The digital signal data corresponding to the autoradiograph may be photoelectrically detected as stimulated emission from the recording of the autoradiograph of the resolved rows on a phosphor sheet or as visible images from the recording by the autoradiograph of the resolved rows on a radiosensitive material.

11 Claims, 5 Drawing Sheets

4,885,696

SIGNAL PROCESSING METHOD FOR DETERMINING BASE SEQUENCE OF NUCLEIC ACID

BACKGROUND OF THE INVENTION

1. Field of the Invention

This invention relates to a signal processing method for determining base sequence of nucleic acids.

2. Description of the Prior Art

It is essential to obtain genetic information carried by organisms in order to make the function or replication mechanism of the organism clear in the field of molecular biology which has been rapidly developed in recent years. Particularly, it is essential to determine base sequence of nucleic acids such as DNA (or DNA fragment; the same applies hereinbelow) which carries specific genetic information.

The Maxam-Gilbert method and Sanger-Coulson method are known as typical methods for determining the base sequence of nucleic acids such as DNA and RNA. In the former Maxam-Gilbert method, a group containing a radioactive isotope such as $^{32}P$ is attached to a chain molecule of DNA or a DNA fragment at one end to label it with the radioactive element and then the bond between the constitutional units of the chain molecule is base-specifically cleaved by a chemical reaction. A mixture of the resulting base-specific DNA cleavage products is resolved (developed) through gel electrophoresis to obtain a resolved pattern (not visible) wherein each of the numerous cleavage products is resolved on the gel support medium. The resolved pattern is visualized on a radiographic film such as an X-ray film to obtain an autoradiograph thereof as a visible image. The bases in certain positional relationships with the end of the radioactive element-attached chain molecule can be sequentially determined according to the visualized autoradiograph and the applied base-specific cleavage means. In this way, the sequence for all bases of the DNA specimen can be determined.

In the latter Sanger-Coulson method, synthetic DNA products which are complementary to the chain molecule of DNA or DNA fragment and radioactively labeled, are base-specifically synthesized by utilizing a chemical reaction, and the obtained mixture of numerous synthetic DNA products is resolved on a support medium by gel electrophoresis to obtain a resolved pattern. In a similar manner to that described above, the base sequence of DNA can be determined according to the visualized autoradiograph.

For the purpose of carrying out the determination of the base sequence of nucleic acids simply with high accuracy in autoradiography, there are described in U.S. patent application Nos. 664,405 and 837,037 autoradiographic procedures which utilize a radiation image recording and reproducing method using a stimulable phosphor sheet, in place of the above-mensioned conventional radiography using a radiosensitive material such as an X-ray film. The stimulable phosphor sheet comprises a stimulable phosphor and has such properties that when exposed to a radiation, the stimulable phosphor absorbs a portion of radiation energy and then emits light (stimulated emission) corresponding to the radiation energy stored therein upon excitation with an electromagnetic wave (stimulating rays) such as visible light or infrared rays. According to this method, exposure time can be greatly shortened and there is no fear of causing problems such as chemical fog associated with the prior art. Further, since the autoradiograph having information on radioactively labeled substances is stored in the phosphor sheet as radiation energy and then read out as stimulated emission in time sequence, information can be expressed by the form of numerals and/or symbols in addition to image.

The base sequence of the nucleic acids has been conventionally determined by visually judging individual resolved positions of the base-specific cleavage products or the base-specific synthetic products of radioactively labeled nucleic acid (hereinafter referred to as simply base-specific fragments of nucleic acid) on the autoradiograph and comparing them among the resolved rows thereof. Namely, the analysis of the autoradiograph is done by observing the visualized autoradiograph with eyes, and such visual analysis requires great amounts of time and labor.

Further, since the visual analysis of the autoradiograph varies or fluctuates owing to the skill of investigators, the results on the determination of the base sequence of nucleic acid vary depending on the investigators and the accuracy of information is limited to a certain extent.

In order to improve the accuracy of the information, there are proposed in U.S. patent application Nos. 568,877 (abandoned), 730,034 (abandoned), 917,606 and 917,609 methods for automatically determining the base sequence of DNA by obtaining the autoradiograph as digital signals and subjecting the digital signals to appropriate signal processing. The digital signals corresponding to the autoradiograph can be obtained either by visualizing the autoradiograph on a radiographic film and photoelectrically reading out the visible image on said film by means of reflected light or transmitted light when the conventional radiography is employed, or by directly reading out the stimulable phosphor sheet without the visualization of the autoradiograph when the radiation image recording and reproducing method is employed.

However, the resolved pattern obtained by resolving (developing) radioactively labeled substances on a support medium by electrophoresis or the like is liable to cause various distortion and noise. When the production and the separation of the base-specific fragments are insufficient during the preparation of a sample, or when the base-specific fragments are mixed with each other during the introduction of the sample into slots, bands (ghost bands or extra bands) happen to appear at positions where any band inherent to the resolved row should not exist. When the sample is contaminated with radioactive impurities, or when a stimulable phosphor sheet or a radiosensitive material is exposed to a natural radiation, noise is produced on the autoradiograph. The bands including such ghost bands are compared with each other, and as a result, an error is caused in the determination of the base sequence to lower the accuracy of the information on the base sequence.

It is highly desired to automatically determine the base sequence of nucleic acids with high accuracy through the signal processing of the digital signals corresponding to the autoradiograph, even when the noise is caused on the autoradiograph.

SUMMARY OF THE INVENTION

The present inventor has accomplished that the base sequence of nucleic acids is automatically determined with easiness and high accuracy by suitably processing digital signals corresponding to the autoradiograph of the resolved pattern even when noise is caused on the autoradiograph.

The present invention provides in one aspect a signal processing method for determining base sequence of nucleic acids by subjecting digital signals to signal processing.

Digital signals corresponding to an autoradiograph of plural resolved rows which are formed by resolving a mixture of base-specific DNA fragments or base-specific RNA fragments labeled with a radioactive element in a one-dimensional direction on a support medium are produced. The present signal processing method determines base sequence by a series of steps which detects bands on the resolved rows corresponding to DNA or RNA bases to be identified. The signal processing method first generates a waveform from the digital signals with peaks representing base position and signal level. A signal level along the waveform and a search-fiducial point on the waveform are selected, and then an interval adjacent to the search-fiducial point is selected. A plurality of domains within the selected interval is defined. Next the mean signal level value of the waveform signal levels in all of the domains is determined, and a threshold signal value based on the mean signal level value is selected. The interval is then searched for peaks with signals greater than the threshold value. If a peak is located, the band corresponding to the nucleic acid base is identified from the peak. The located peak then becomes the next search-fiducial point, and a new interval is selected and searched for peaks until all the bands have been identified. If no peak is located, a new search point is selected, and the process is repeated until the entire waveform has been searched for peaks.

In another aspect of the present signal processing method, at least two waveforms are generated, and the process steps outlined above are conducted in sequence for each waveform until all bands on a resolved row have been identified.

According to the present invention, the base sequence of nucleic acids can be simply determined with high accuracy by processing the digital signals corresponding to the autoradiograph of a resolved pattern which is formed by resolving a mixture of the base-specific fragments of a nucleic acid on a support medium, through an appropriate signal processing circuit having a feature capable of eliminating noise and detecting only intrinsic bands, even when the resolved pattern causes noise.

The first method of the present invention resolves the following problem with respect to the extra bands. The image density (level of digital signal) of noise and extra bands appearing on the autoradiograph, due to the mixing of a sample or the natural radiation, is generally lower than that of the intrinsic bands. However, in the Sanger-Coulson method, the amount of radioactive element is increased and the intensity of radioactivity becomes higher in proportion as the molecular weight of the base-specific fragments of the sample is increased. There is produced on the autoradiograph a density gradient (change of signal level) so that the image density is lowered as the migration distance becomes greater.

Consequently, the identification of bands is subject to error. An extra band may be detected as an intrinsic band, an intrinsic band may be erroneously eliminated, or the identification of a band as intrinsic based on the comparison of peak signal level to a preset signal level may not be made correctly. The accurate information on the base sequence of nucleic acids can not be obtained.

According to the first method of the present invention, only intrinsic bands can be completely detected on the basis of a threshold value which fluctuates from interval to interval, by calculating the mean value of signal levels for every interval and setting the threshold value which enables intrinsic band to be separated from noise for each interval based on the mean value. The base sequence of nucleic acids can be determined with high accuracy and easiness by comparing the detected bands among the resolved rows on the basis of the band positions.

The second method of the present invention resolves the following problem with respect to the noise. It is possible to mistake noise for band in the determination of bands, when peaks are only detected on a one-dimensional waveform (raster) composed of position along the resolving direction and signal level for the resolved row, and the accurate information on the base sequence of nucleic acids can not be obtained. Usually, the band has a width in a direction perpendicular to the resolving direction depending on the size of slot. On the other hand, the noise appearing on an autoradiograph due to the incomplete introduction of a radioactive element into a sample during the preparation of the sample or the incorporation of a natural radiation during the exposure, is in the form of a spot or a band the width of which is narrower than that of an intrinsic band.

According to the second method of the present invention, only intrinsic bands can be detected by excluding noise in such a manner that there are prepared many rasters for each resolved row and determination is made on whether the detected peaks are ones for intrinsic bands or noise, based on decision on whether the peaks continuously exist on these rasters in a direction perpendicular to the resolving direction or not. The base sequence of nucleic acids can be simply determined with high accuracy by comparing the detected bands among the resolved rows on the basis of the band positions.

DETAILED DESCRIPTION OF THE INVENTION

Figure 1:
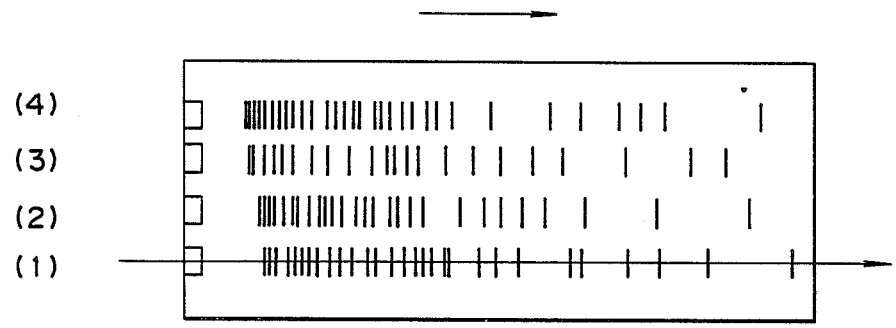
FIG. 1 shows an example of the autoradiograph of an electrophoretic pattern which causes a density gradient.

Examples of samples employable in the present invention include mixtures of base-specific fragments of nucleic acids such as DNA and RNA labeled with a radioactive element. The term "fragments" of nucleic acids mean portions of a long-chain molecule. For instance, a mixture of base-specific DNA cleavage products, which is a kind of a mixture of base-specific DNA fragments, can be obtained by base-specifically cleaving the radioactively labeled DNA according to the aforementioned Maxam-Gilbert method. A mixture of base-specific DNA synthetic products can be obtained by synthesizing from radioactively labeled deoxynucleoside triphosphates and DNA polymerase by use of DNA as a template according to the aforementioned Sanger-Coulson method.

Mixtures of base-specific RNA fragments can be also obtained as a mixture of cleavage products or a mixture of synthetic products in the similar manner to the DNA methods. DNA is composed of four kinds of bases: adenine, guanine, thymine and cytosine as its constitutional units, and RNA is composed of four kinds of bases: adenine, guanine, uracil and cytosine. These substances can be labeled with a radioactive element such as $^{32}P$, $^{14}C$, $^{35}S$, $^{3}H$ or $^{125}I$ by any of appropriate methods.

A sample, which is a mixture of the base-specific fragments of a nucleic acid labeled with a radioactive element, can be resolved (developed) on a known support medium such as a gel support medium by any of conventional resolving (developing) procedures such as electrophoresis, thin layer chromatography, column chromatography and paper chromatography.

The support medium on which the radioactively labeled substances are resolved, is autoradiographed by means of the conventional radiography using a radiosensitive material or the radiation image recording and reproducing method using a stimulable phosphor sheet. The digital signals corresponding to the autoradiograph are then obtained through an appropriate read-out system.

When the conventional radiography is used, the support medium and a radiosensitive material such as an X-ray film are placed together in layers at a low temperature or at room temperature for a long period of time (several hours to several tens of hours) to expose the radiographic film. The radiographic film is then developed to visualize the autoradiograph of the radioactively labeled substances on the film, and the visualized autoradiograph is read out by using an image read-out system. For instance, the radiographic film is irradiated with an optical beam and the beam transmitted thereby or reflected therefrom is photoelectrically detected, whereby the visualized autoradiograph can be transformed to electric signals. Further, the electric signals are converted into digital signals corresponding to the autoradiograph through A/D conversion.

When the radiation image recording and reproducing method is used, the support medium and the stimulable phosphor sheet are placed together in layers at an ambient temperature for a short period of time (several seconds to several tens of minutes) to store radiation energy radiating from the radioactively labeled substances in the phosphor sheet, whereby the autoradiograph is recorded as a kind of a latent image (energy-stored image) on the phosphor sheet. The stimulable phosphor sheet, for instance, has a basic structure where a support comprising a plastic film, a phosphor layer comprising a stimulable phosphor such as a divalent europium activated barium fluorobromide phosphor (BaFGr:Eu$^{2+}$) and a transparent protective film are laminated in this order. The stimulable phosphor has characteristics of absorbing and storing radiation energy when irradiated with a radiation such as X-rays and subsequently releasing the stored radiation energy as stimulated emission when excited with visible light to infrared rays.

Then, the autoradiograph stored and recorded on the stimulable phosphor sheet is read out by using a read-out system. For instance, the phosphor sheet is scanned with a laser beam to release the radiation energy stored in the stimulable phosphor as light emission and the emitted light is photoelectrically detected, so that the autoradiograph can be directly obtained as electric signals without the visualization thereof. Further, the electric signals are converted into digital signals corresponding to the autoradiograph through A/D conversion.

The above-described methods for measuring the autoradiograph and obtaining the digital signals corresponding thereto are described in more detail in the aforementioned U.S. patent application Nos. 568,877 (now abandoned) and 837,037.

While the methods for obtaining the digital signals corresponding to the autoradiograph using the conventional radiography and the radiation image recording and reproducing method are described above, the present invention is not limited thereto and digital signals obtained by any other methods can be applied to the signal processing method of the invention, provided that they correspond to the autoradiograph.

In the above read-out procedures, it is not always necessary to conduct the read-out operation of the autoradiograph all over the surface of the radiographic film or the stimulable phosphor sheet. Only the image region may be subjected to the read-out operation.

In the present invention, there may be previously inputted information on the location of each resolved row and the width of each band to preset read-out conditions and then conducted scanning at a scanning line density such that each band is traversed by at least one or at least two of the scanning lines in the read-out operation, so as to shorten read-out time and obtain efficiently necessary information. The digital signals corresponding to the autoradiograph in the invention also include the thus-obtained digital signals.

The obtained digital signals $D_{xy}$ comprise a coordinate (x,y) which is represented by a coordinate system fixed to the radiographic film or the stimulable phosphor sheet and a signal level (z) at the coordinate. The signal level represents the density of image at the coordinate, that is, the amount of the radioactively labeled substances. Accordingly, a series of the digital signals (namely, digital image data) have information on two-dimensional location of the labeled substances.

The digital signals corresponding to the autoradiograph of the radioactively labeled substances resolved on a support medium, is subjected to signal processing to determine the base sequence of nucleic acid according to the invention described in more detail below.

Now, the first signal processing method of the present invention will be described by referring to an example of an electrophoretic pattern formed with a combination of the following four groups of base-specific DNA fragments labeled with a radioactive element:

(1) guanine (G)—specific DNA synthetic products,
(2) adenine (A)—specific DNA synthetic products,
(3) thymine (T)—specific DNA synthetic products,
(4) cytosine (C)—specific DNA synthetic products.

Each group of the base-specific DNA synthetic products is composed of DNA products which are synthesized according to the Sanger-Coulson method and have various lengths and the same base at terminals.

FIG. 1 shows an autoradiograph of the electrophoretic pattern obtained by electrophoresing the above four groups of the base-specific DNA synthetic products in four slots, respectively. On the autoradiograph, there is produced a density gradient along the resolving direction (in the direction of an arrow).

The digital signals corresponding to the autoradiograph are stored temporarily in a memory device of the signal processing circuit (that is, stored in a nonvolatile memory unit such as a buffer memory, a magnetic disk, etc.).

In the first place, there is prepared a one-dimensional waveform composed of position along the resolving direction and signal level for each resolved row (lane).

Figure 2:
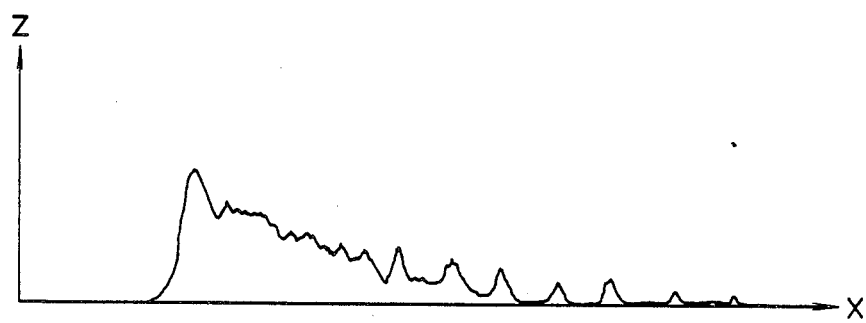
FIG. 2 shows a one-dimensional waveform for the first lane along the arrow shown in FIG. 1.

FIG. 2 shows a one-dimensional waveform for the first lane prepared by extracting digital signals in the direction of the arrow shown in FIG. 1. FIG. 2 corresponds to the sectional view of image density for the first lane.

Figure 3:
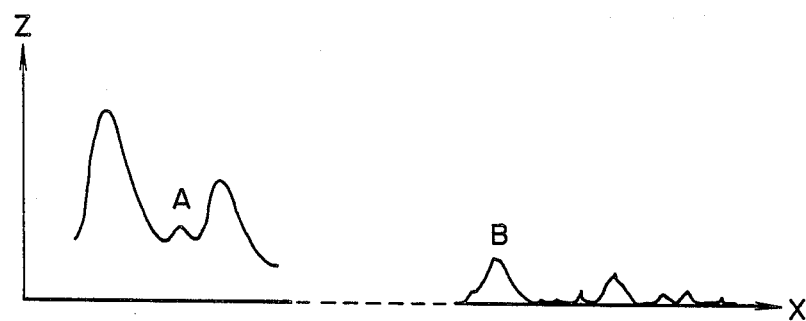
FIG. 3 is a partial enlarged view of FIG. 2.

FIG. 3 is a partial enlarged view of FIG. 2. In FIG. 3, the left part is a zone near to the electrophoresis-starting position, and the peak A (at which the signal level is maximum) is lower than peaks on both sides thereof so that the peak A is clearly an extra band or noise. The right part is a zone (where the migration distance is long) far away from the electrophoresis-starting position, and the peak B is recognized as an intrinsic band in comparison with other peaks. However, when the peak A is compared with the peak B, the signal level of the peak A is higher than that of the peak B. It will be understood that determination on whether a peak is an intrinsic band or not should not be made simply from the signal level (absolute value) of each peak. It is necessary that relative comparison must be made by taking signal levels around the peak to be detected into consideration.

Figure 4:
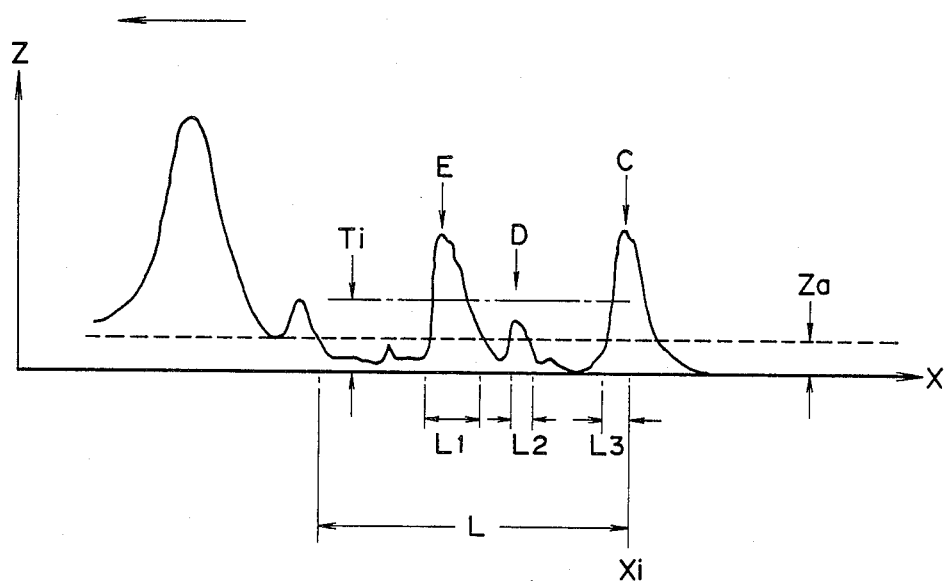
FIG. 4 is another partial enlarged view of FIG. 2, showing an embodiment of the method of the present invention.

FIG. 4 is a partial enlarged view of the one-dimensional waveform of FIG. 2, and shows an embodiment illustrating the essential features of the present invention relating to the determination of threshold value and the detection of bands on the basis of the threshold value.

The subsequent processing for the detection of bands will be described by referring to FIG. 4.

In the second place, there is calculated the mean value $Z_i$ of signal levels Z within a given interval L from the fiducial point $x_i$ of the band search on the one-dimensional waveform.

The search-fiducial point $x_i$ is the position of the peak C which is an already determined intrinsic band, in FIG. 4. Usually, the first search-fiducial point is preferably the lowermost end of electrophoresis at the longest migration distance (the right end of FIG. 2), where the space between bands is large and the search is preferably made from the lower end of electrophoresis toward the upper end in order.

The interval L may be previously set to a constant on the basis of the probable migration distance (i.e., the practical length of the support medium), or may be set as an appropiate function of migration distance (or of position along the electrophoretic direction) so as to allow it to vary depending on the search position. In the latter case, the number of peaks to be detected within one interval is made approximately constant, irrespective of the search position. The interval L may be started from the fiducial point $X_i$ in the search direction [in the direction of an arrow (←)] as shown in FIG. 4, or the interval L may be taken by ½ L on each of both sides of the fiducial point.

The mean level value $Z_i$ can be obtained by calculating the mean value of signal levels in the domains where signal levels are not less than a given value $Z_a$, that is, in the domains $L_1$, $L_2$ and $L_3$. Namely, the mean value of signal levels of not less than $Z_a$ is obtained. Hence, relatively small extra bands and noise (background noise) appearing on the whole of the electrophoretic pattern can be removed.

In the third place, a threshold value $T_i$ is determined on the basis of the mean level value $Z_i$. The threshold value $T_i$ is obtained by substituting $Z_i$ for a preset function in which a variable is the mean value $[T_i=f(Z_i)]$. For instance, the following formula is given.

$$T_i = \alpha Z_i$$

wherein coefficient $\alpha$ is a positive number excluding zero. In this way, the threshold value $T_i$ is set to a proper value which enables extra bands and intrinsic bands to be separated from each other. In the case that the coefficient $\alpha$ is set to a constant larger than 1, extra bands can be excluded even when the peak of the extra band is relatively large, or even when many extra bands exist. The function $f(Z_i)$ or the coefficient $\alpha$ may be an appropriate function of migration distance so as to allow it to vary depending on the search position.

In the fourth place, the interval L from the search-fiducial point $x_i$ is searched for peak(s) at which signal level is not less than the threshold value $T_i$. A peak is a point having the maximum signal level on the one-dimensional waveform. Only the domains $L_1$ to $L_3$ where signal levels are not less than the value $Z_a$ may be searched for peak instead of making the search over the whole interval L, to shorten the search time.

In the fifth place, peak(s) at which signal level is not less than the threshold value $T_i$ is determined to be intrinsic band(s), and peak(s) at which signal level is below $T_i$ is decided to be extra band(s) or noise and is ignored. In FIG. 4, there are two peaks D and E in the domains $L_1$ to $L_3$. Only the peak E at which signal level exceeds $T_i$ is determined to be an intrinsic band, and the peak D is excluded as an extra band.

When the detection of band in the interval L is completed, the position of the peak E (intrinsic band) of the level above the threshold value $T_i$ is allowed to be the next search-fiducial point $x_{i+1}$. The above-described procedures are repeated in the next interval L from the fiducial point $x_{i+1}$. When there exist two or more peaks of the level above $T_i$, the peak nearest to the fiducial point in the search direction may be chosen as the next fiducial point, to determine intrinsic bands with much higher accuracy by taking a little change in circumferential signal levels into consideration while slightly shifting the interval. The farthest peak from the fiducial point in the search direction may be chosen, to reduce the number of times of the band-search procedure and to short the processing time by decreasing the overlap of the intervals.

When no peak (intrinsic band) at which the signal level is not less than the threshold value $T_i$ exists, a position at a given distance dL from the search-fiducial point $x_i$ is allowed to be the next search-fiducial point $x_{i+1}$. The above-described procedures are then repeated. The distance dL may be previously set to a constant value such as a length corresponding to one pixel, or may be set as a function of migration distance and determined on the basis of the fiducial point.

The procedures described above are repeatedly conducted to the electrophoresis-starting point (the left end of FIG. 2), to detect all intrinsic bands on the first lane. Further, the other three lanes are subjected to the above procedures to thereby detect all intrinsic bands on the electrophoretic pattern.

The second signal processing method of the present invention will be described by referring to another example of the electrophoretic pattern formed with a combination of the following four groups of radioactively labeled base-specific DNA fragments:

(1) guanine (G)—specific DNA fragments,
(2) adenine (A)—specific DNA fragments,
(3) thymine (T)—specific DNA fragments,
(4) cytosine (C)—specific DNA fragments.

Each group of the base-specific DNA fragments is composed of base-specific cleavage products or synthetic products which have various lengths and the same base at terminals.

Figure 5:
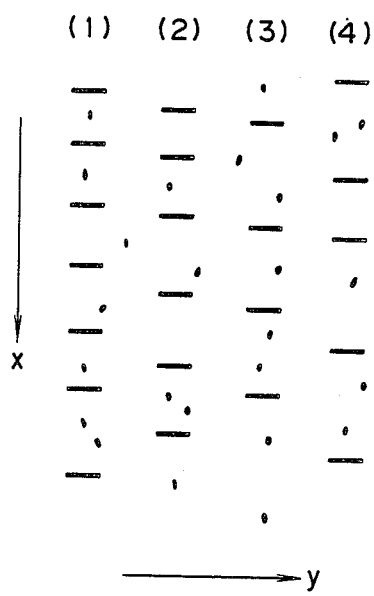
FIG. 5 shows an example of the autoradiograph of an electrophoretic pattern which causes noise.

FIG. 5 shows an autoradiograph of the electrophoretic pattern obtained by electrophoresing the above four groups of the base-specific DNA fragments in four slots, respectively. The electrophoretic direction is in the x-direction.

In the first place, at least two one-dimensional waveforms (rasters) composed of position along the electrophoretic direction and signal level for each electrophoretic row (lane) are prepared on the basis of the digital image data corresponding to the autoradiograph.

When the digital image data are obtained by scanning in the electrophoretic direction in such a scanning line density that at least two scanning lines traverse each band as afore-described, the raster composed of position (x) and signal level (z) can be directly prepared for every scanning line. When the whole of the autoradiograph is read out, the similar operation is conducted on the image data to extract signals along each lane to prepare rasters.

The number of rasters per lane varies depending on the shape (width) of the slot, the amount of the sample and the number of pixels, and is generally 5 to 40 from the viewpoint of the accuracy of band detection. For instance, when the width of the slot is 5 mm, the space between pixels is 0.2 mm and the space between rasters (prepared by pixel unit) is also 0.2 mm, the number of rasters per lane is 25.

Figure 6:
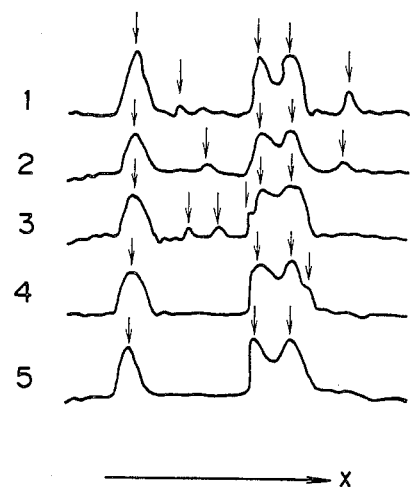
FIG. 6 is a partial view showing rasters for the first lane.

FIG. 6 partially shows many rasters prepared for the first lane. The raster represents a sectional view of image density obtained by cutting the first lane off at every position in the x-direction.

In the second place, peaks on all the rasters are detected. The peak is detected, for instance, by finding out a position at which a sign of difference in signal level is inverted.

In FIG. 6, each arrow (←) indicates a peak.

In the third place, a peak on an arbitrary raster is chosen and search for a peak is made in a given domain centering a position corresponding to the chosen peak position on a raster adjoining the chosen raster. In the fourth place, the search of the peak is repeatedly made on the adjoining rasters included in the same lane in order, so long as a peak is found.

The domain is usually a domain of $Y_a \pm \sigma$ mm centering the peak position $Y_a$, wherein $\sigma$ is set depending on the space between rasters. For instance, when the raster space is 0.2 mm, $\sigma = 0.4$. By limiting the domain of the peak search, it is decided that a band exists only at the positions of peaks which are found on plural rasters without being so deviated from one another in the electrophoretic direction. The accuracy of the band detection can be improved.

The peak search may be made on every one adjoining raster, or simultaneously on two or more rasters. For instance, the search can be made simultaneously on two to five rasters. The simultaneous search on plural rasters is preferred, when there is an interruption in peak appearance.

Figure 7:
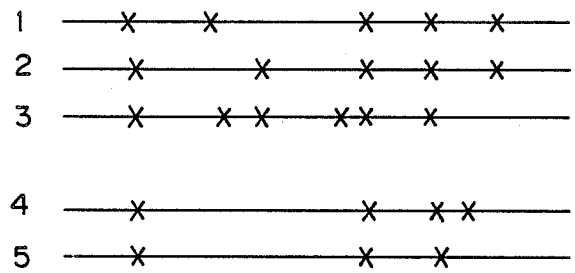
FIG. 7 is a diagram showing the existence of peaks on the rasters of FIG. 6.

FIG. 7 is a diagram showing the existence of peaks on each raster, wherein the sign X represents a peak position.

In the fifth place, determination whether a series of the peaks found within a given domain ($Y_a \pm \sigma$) is a band or not is made on the basis of decision on the continuity of the peaks.

A criterion for the decision on the continuity of the peaks varies depending upon the width of the band (i.e., the width of the slot), the shape of the pattern and the space between the rasters. It is generally determined that a band exists at a series of the peak positions, in the case that the peaks are continuously found on N rasters or more, wherein N is an integer in a range of $13 \leq N \leq 37$ when the width of the slot is 5 mm and the raster space is 0.2 mm (the number of rasters per lane being 25), by taking the stretching of band in the width direction in electrophoresis into consideration.

Preferably, the determination of the band existence is made in the case of peaks being continuously found on rasters ranging from N to M. For instance, N=15 and M=30 under the above conditions.

There is a possibility that a series of peaks are not continuously found on rasters, when peaks are not sharp or signal levels are locally low. It is preferred that the determination of the band existence is also made in the case that the interruption in peak appearance (the existence of a raster on which no peak is found) for a series of rasters peak-searched is within a given limit. When the interruption in peak appearance occurs at L positions or less and the number of rasters on which no peak is found at each interrupted position, is K or less, the determination of the band existence is made at a series of the peak positions. K and L are set depending on the raster space and for instance, are integers in ranges of $1 \leq K \leq 3$ and $1 \leq L \leq 3$ when the raster space is 0.2 mm.

The determination that a band does not exist at peak position(s) is made outside the cases specified above.

Figure 8:
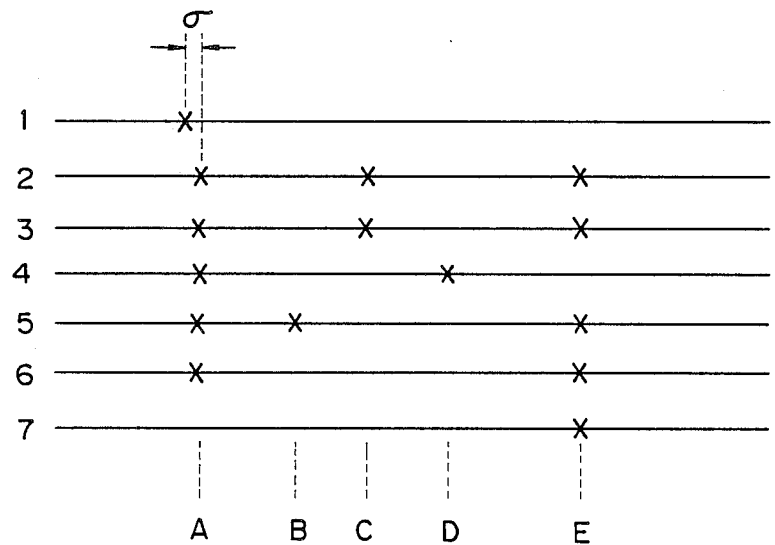
FIG. 8 is a diagram showing the existence of peaks on other rasters.
Figure 9:
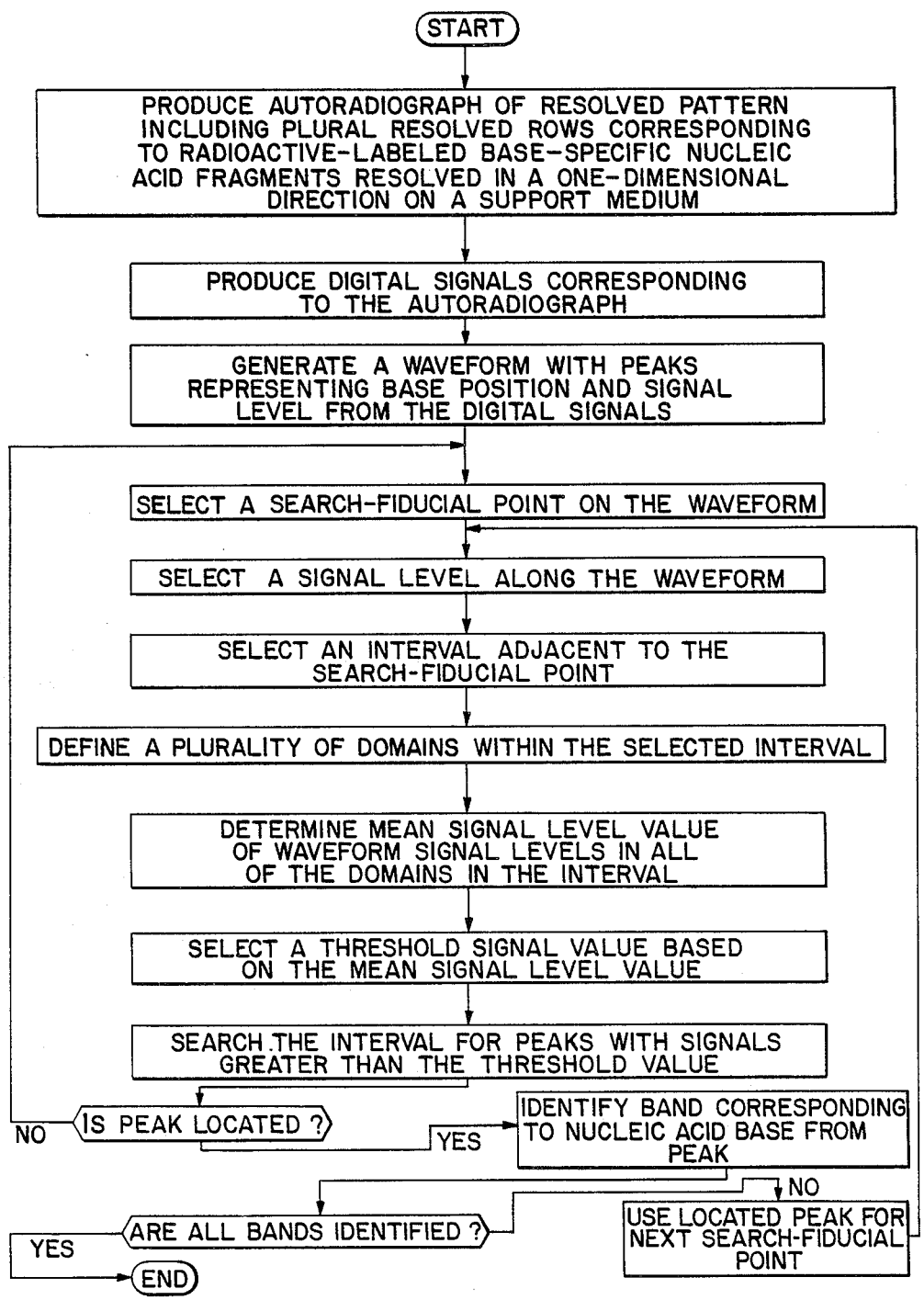
FIG. 9 is a flowchart representing the method of the present invention.

FIG. 8 is another diagram showing the existence of peaks on plural rasters, wherein the sign X represents a peak position.

In FIG. 8, it is determined that series of the peaks A and E are respectively bands and the other peaks B, C and D are not bands but noise.

All the peaks on said raster and other rasters of the first lane are subjected to the above-described procedures to detect all bands on the first lane. Further, all peaks on the rasters of the other three lanes are subjected thereto to detect all bands on the electrophoretic pattern. In this way, the bands can be detected with high accuracy, even when the electrophoretic pattern causes noise.

When the electrophoretic pattern causes a smiling phenomenon, various distortions such as offset distortion and combining of some bands, or noise, signal processing for correction thereof may be made before or after the determination of the band positions.

The smiling phenomenon is a phenomenon in which migration distances of the radioactively labeled substances at the both sides of the support medium are shorter than that in the vicinity of the center thereof. The smiling phenomenon is caused by heat dissipation effect (so-called edge effect), etc. during the electrophoresis. The offset distortion is a phenomenon in which positions of the lanes are wholly deviated from one another and is caused by difference between the slots in the electrophoresis-starting position or time of samples, which is due to the unevenness of the shapes of slots, etc. The combining of bands is a phenomenon in which two or three bands are combined together to form one broad band and is caused by insufficient electrophoresis. Usually, the combined bands tend to appear in the upper region of the pattern near to the electrophoresis-starting position.

The signal processing methods for the correction for the smiling phenomenon, the offset distortion and the combining of bands are described in our co-pending Japanese Patent Application Nos. 60(1985)-74899, 60(1985)-74900, 60(1985)-85275, 60(1985)-85276, 60(1985)-111185 and 60(1985)-111186 (the whole content of which corresponds to U.S. patent application Nos. 849,187, 854,381 and 866,355).

All the bands are sequenced immediately by comparing the determined band positions with one another. The sequence can be easily determined by utilizing the fact that there do not exist two or more bands at the corresponding positions on different lanes, since the combination of the above four groups of the base-specific DNA fragments is exclusive. Since the slots (1) to (4) have information on the terminal bases of (G), (A), (T) and (C), respectively, the base sequence of DNA is obtained by substituting the bands with bases corresponding to the slots which the individual bands belong to. For instance, the following base sequence of DNA can be obtained.

A—G—C—T—A—A—G— . . .

Thus, the base sequence of one chain molecule of DNA can be determined. The representation mode of the information on the base sequence of DNA is by no means limited to the above-mentioned mode, and other representation modes may be utilized. For instance, the intensity (z') of each band can be represented as the relative amount of the radioactively labeled substances, if desired. Further, the base sequence of both chain molecules of DNA can be also represented.

Information on the base sequence of DNA can be also displayed as an image on the basis of the above processed digital signals. At the same time, the original autoradiograph can be displayed as a visible image. In this case, investigators themselves can finally determine the DNA sequence on the basis of the display image.

In the above-mentioned example, there has been described the case where the exclusive combination of the mixture (G, A, T, C) of base-specific DNA fragments as a sample is used, but the signal processing method of the present invention is by no means limited to said combination, and other combinations can be used. For instance, a combination of (G, G+A, T+C, C) may be used. Further, the method of the invention can be also applied to the mixtures (for instance, a combination of G, A, U, C) of base-specific RNA fragments. The detection of bands is not limited to resolved rows of one combination of base-specific fragments of a nucleic acid, but can be made for the whole resolved rows simultaneously resolved on a support medium.

It is possible to perform genetic philological information processing such as a comparison between the obtained base sequence of the DNA and the base sequence of another DNA which has been already recorded and stored in a suitable means.

The information on the base sequence of DNA determined through the above-described signal processing is output from the signal processing circuit and subsequently transmitted to a recording device directly or optionally via storage in a storing means such as a magnetic disk or a magnetic tape.

Various recording devices based on various systems can be employed for the above-described purpose, for instance, a device for visualizing optically by scanning a photosensitive material with laser beam, etc., a display means for visualizing electrically on CRT, etc., a means for printing a radiation image displayed on CRT by means of a video printer, and a means for visualizing on a heatsensitive recording material using thermic rays.

I claim:

1. A method for determining the base sequence of a nucleic acid by obtaining digital signals corresponding to an autoradiograph of a resolved pattern including plural resolved rows consisting of four rows formed by resolving each of four groups of a mixture of base-specific nucleic acid fragments on a support medium labeled with a radioactive element that have migrated in a one-dimensional migration direction on the support medium and processing the digital signals thus obtained to determine the nucleic acid base sequence, wherein the digital signal processing method includes the steps of:

(a) generating from said digital signals a waveform including peaks representative of base position in the resolving direction and the signal level for each resolved row;
  (b) selecting a search-fiducial point, an interval adjacent to said search-fiducial point, and a signal level on the waveform;
  (c) defining a plurality of domains within said interval;
  (d) first determining a mean signal level value of the waveform signal levels in said domains and then selecting a threshold signal value based on the mean signal signal level value;
  (e) searching the interval to locate a peak having a signal level greater than the threshold signal value and, if a peak is located, identifying a band corresponding to a nucleic acid base at the position of the peak, wherein the located peak is then selected to be the next search-fiducial point and steps (b)-(e) are repeated to identify all of said bands on the resolved rows; or, if no peak is located, selecting a new search-fiducial point a predetermined distance from said original search-fiducial point; and
  (f) determining the nucleic acid base sequence from the sequence of the bands identified in step (e).

2. The method as claimed in claim 1, wherein said given interval and said given level in the step (b), said threshold value in the step (c) and said given distance in the step (e) are set depending on the position on the one-dimensional waveform, respectively.

3. The method as claimed in claim 1, wherein said digital signals corresponding to the autoradiograph are obtained by placing the support medium and a stimulable phosphor sheet comprising a stimulable phosphor together in layers to record the autoradiograph of the resolved rows on the phosphor sheet as an energy-stored image, irradiating said phosphor sheet with stimulating rays and photoelectrically detecting the autoradiograph as stimulated emission.

4. The method as claimed in claim 1, wherein said digital signals corresponding to the autoradiograph are obtained by placing the support medium and a radiosensitive material together in layers to record the autoradiograph of the resolved rows on the radiosensitive material as a visible image and photoelectrically reading out the autoradiograph visualized on said radiosensitive material.

5. The method as claimed in claim 1, wherein the nucleic acid is DNA and the four groups of base-specific fragments consist of:
   (1) guanine-specific DNA fragments;
   (2) adenine-specific DNA fragments;
   (3) thymine-specific DNA fragments; and
   (4) cytosine-specific DNA fragments.

6. The method as claimed in claim 1, wherein the search-fiducial point selected in step (b) is located at the greatest distance along the one-dimensional migration direction and step (e) is conducted in the direction opposite to the resolution direction.

7. The method as claimed in claim 1, wherein the peak nearest to the selected search-fiducial point becomes the next search-fiducial point.

8. A signal processing method for determining the base sequence of a nucleic acid by obtaining digital signals corresponding to an autoradiograph of a resolved pattern including plural resolved rows consisting of four rows formed by resolving each of four groups of a mixture of base-specific nucleic acid fragments on a support medium labeled with a radioactive element in a one-dimensional direction on the support medium and processing the digital signals thus obtained to determine the nucleic acid base sequence, wherein said digital signal processing method includes the steps of:
   (a) generating from said digital signals at least two adjacent waveforms representative of base position in the resolving direction and the signal level for each resolved row;
   (b) identifying the peaks on each of the waveforms;
   (c) selecting one peak on one of the waveforms;
   (d) searching a given domain on either side of the selected peak to determine the existence of a peak on an adjacent waveform having a center corresponding to the center of the selected peak;
   (e) repeating step (d) to search each adjacent waveform generated in step (a);
   (f) determining the existence or nonexistence of a band corresponding to a nucleic acid base based on the presence or absence, respectively, of a series of corresponding peaks located on adjacent waveforms in steps (d) and (e); and
   (g) repeating sequentially steps (c), (d), (e) and (f) until all of the bands on a resolved row have been detected.

9. The signal processing method as claimed in claim 8, wherein said digital signals corresponding to the autoradiograph are obtained by placing the support medium and a stimulable phosphor sheet comprising a stimulable phosphor together in layers to record the autoradiograph of the resolved rows on the phosphor sheet as an energy-stored image, irradiating said phosphor sheet with stimulating rays and photoelectrically detecting the autoradiograph as stimulated emission.

10. The signal processing method as claimed in claim 8, wherein said digital signals corresponding to the autoradiograph are obtained by placing the support medium and a radiosensitive material together in layers to record the autoradiograph of the resolved rows on the radiosensitive material as a visible image and photoelectrically reading out the autoradiograph visualized on said radiosensitive material.

11. The signal processing method as claimed in claim 8, wherein the nucleic acid is DNA and the four groups of base-specific fragments consist of:
   (1) guanine-specific DNA fragments;
   (2) adenine-specific DNA fragments;
   (3) thymine-specific DNA fragments; and
   (4) cytosine-specific DNA fragments.

* * * * *